(12) United States Patent
Chen et al.

(10) Patent No.: US 11,896,355 B2
(45) Date of Patent: Feb. 13, 2024

(54) BLOOD PRESSURE TRACKING AND DETECTION SYSTEM

(71) Applicant: Tiangong University, Tianjin (CN)

(72) Inventors: Ruijuan Chen, Tianjin (CN); Shumian Xiao, Tianjin (CN); Cong Wang, Tianjin (CN); Huiquan Wang, Tianjin (CN)

(73) Assignee: Tiangong University, Tianjin (CN)

( * ) Notice: Subject to any disclaimer, the term of this patent is extended or adjusted under 35 U.S.C. 154(b) by 0 days.

(21) Appl. No.: 17/960,337

(22) Filed: Oct. 5, 2022

(65) Prior Publication Data
US 2023/0371830 A1 Nov. 23, 2023

(51) Int. Cl.
*A61B 5/022* (2006.01)
*A61B 5/00* (2006.01)

(52) U.S. Cl.
CPC ........ *A61B 5/02225* (2013.01); *A61B 5/7203* (2013.01); *A61B 5/7225* (2013.01); *A61B 5/7246* (2013.01)

(58) Field of Classification Search
CPC . A61B 5/02225; A61B 5/7203; A61B 5/7225; A61B 5/7246
See application file for complete search history.

(56) References Cited

FOREIGN PATENT DOCUMENTS

| CN | 103690152 A | 4/2014 |
|---|---|---|
| CN | 107405090 A | 11/2017 |
| CN | 109717854 A | 5/2019 |
| CN | 113509160 A | 10/2021 |

*Primary Examiner* — Serkan Akar
(74) *Attorney, Agent, or Firm* — Marcus C. Dawes

(57) ABSTRACT

A blood pressure tracking and detection system. The pressure application and release module is configured to apply a pressure to a detected part of a target user according to a pressure application instruction. The pressure application and release module is further configured to release the pressure on the detected part of the target user according to a pressure release instruction. The signal obtaining module is connected to the pressure application and release module. The signal obtaining module is configured to obtain a photoplethysmography (PPG) signal and a pressure signal of the detected part of the target user. The blood pressure tracking and detection module is connected to the signal obtaining module. The blood pressure tracking and detection module is configured to determine an initial blood pressure of the detected part of the target user according to a PPG signal and a pressure signal in a pressure application and release cycle.

4 Claims, 4 Drawing Sheets

BLOOD PRESSURE TRACKING AND DETECTION SYSTEM

CROSS-REFERENCE TO RELATED APPLICATION

This patent application claims the benefit and priority of Chinese Patent Application No. 202210540885.9, filed with the China National Intellectual Property Administration on May 19, 2022, the disclosure of which is incorporated by reference herein in its entirety as part of the present application.

TECHNICAL FIELD

The present disclosure relates to the technical field of biological signal detection, and in particular, to a blood pressure tracking and detection system.

BACKGROUND

Blood pressure is a hemodynamic parameter, and is a beat-to-beat fluctuation under the interaction of vasomotion, arterial mechanisms, and neuromodulation. In clinical practice, the hemodynamic status of the patient can be timely grasped through blood pressure tracking and detection, and complications caused by persistent abnormal blood pressure during surgery can be timely avoided. In daily life, a large number of studies have revealed the necessity of ambulatory blood pressure, especially the necessity of monitoring blood pressure at night.

At present, the system used for blood pressure tracking and detection has shortcomings such as low measurement accuracy, frequent calibration, and complicated operation in long-term blood pressure tracking and detection.

SUMMARY

An objective of the present disclosure is to provide a blood pressure tracking and detection system, so as to overcome shortcomings of an existing blood pressure tracking and detection system such as the inability to stably track and update the blood pressure for a long time, the need for frequent calibration, the need for user interaction during night tracking, and the inability to realize automatic adjustment and tracking.

In order to achieve the above objective, the present disclosure provides the following technical solutions:

A blood pressure tracking and detection system is provided, including: a pressure application and release module, a signal obtaining module, and a blood pressure tracking and detection module.

The pressure application and release module is configured to apply a pressure to a detected part of a target user according to a pressure application instruction. The pressure application and release module is further configured to release the pressure on the detected part of the target user according to a pressure release instruction.

The signal obtaining module is connected to the pressure application and release module. The signal obtaining module is configured to obtain a photoplethysmography (PPG) signal and a pressure signal of the detected part of the target user.

The blood pressure tracking and detection module is connected to the signal obtaining module. The blood pressure tracking and detection module is configured to determine an initial blood pressure of the detected part of the target user according to a PPG signal and a pressure signal in a pressure application and release cycle, so as to determine an initial pressure corresponding to the initial blood pressure, and obtain morphological features of the PPG signal according to the corresponding PPG signal when the pressure signal applied by the pressure application and release module to the detected part of the target user is equal to the initial pressure, so as to update the pressure according to the morphological features.

Optionally, the pressure application and release module may include: a pressure application sub-module and a pressure release sub-module.

The pressure application sub-module may be configured to apply the pressure to the detected part of the target user according to the pressure application instruction.

The pressure release sub-module may be connected to the pressure application sub-module. The pressure release sub-module may be configured to release the pressure on the detected part of the target user according to the pressure release instruction.

Optionally, the pressure application and release module may further include: a deflation speed determination sub-module.

The deflation speed determination sub-module may be connected to the signal obtaining module. The deflation speed determination sub-module may be configured to determine a peak-to-peak value of the PPG signal according to the PPG signal during deflation, and determine a deflation speed according to the peak-to-peak value of the PPG signal.

Optionally, the signal obtaining module may include: an obtaining sub-module, a preprocessing sub-module, and a templating processing sub-module.

The obtaining sub-module may be connected to the pressure application and release module. The obtaining sub-module may be configured to obtain the PPG signal and the pressure signal of the detected part of the target user.

The preprocessing sub-module may be connected to the obtaining sub-module. The preprocessing sub-module may be configured to perform baseline drift removal, noise filtering, envelope detection, and peak-to-peak value detection on the PPG signal.

The templating processing sub-module may be connected to the preprocessing sub-module. The templating processing sub-module may be configured to determine a template waveform of the PPG signal according to the preprocessed PPG signal.

Optionally, the templating processing sub-module may include: a normalization processing unit and a PPG signal template waveform determination unit.

The normalization processing unit may be connected to the PPG signal template waveform determination unit.

The normalization processing unit may be configured to perform single-cycle amplitude and length normalization on the preprocessed PPG signal.

The PPG signal template waveform determination unit may be configured to determine the template waveform of the PPG signal according to a moving average of the PPG signal subjected to single-cycle amplitude and length normalization.

Optionally, the blood pressure tracking and detection module may include: an initial blood pressure calculation sub-module, a pressure maintenance sub-module, a feature extraction sub-module, a feature matching sub-module, and a blood pressure update sub-module.

The initial blood pressure calculation sub-module may be connected to the preprocessing sub-module and the pressure maintenance sub-module.

The initial blood pressure calculation sub-module may be configured to determine a pressure signal applied to the detected part of the target user corresponding to a maximum peak-to-peak difference of the preprocessed PPG signal according to the preprocessed PPG signal and the pressure signal. The pressure signal applied to the detected part of the target user corresponding to the maximum peak-to-peak difference may be the initial pressure of the detected part of the target user, and an initial systolic pressure and an initial diastolic pressure of the detected part of the target user may further be determined according to the initial pressure of the detected part of the target user and the pressure signal in the pressure release instruction.

The pressure maintenance sub-module may be connected to the obtaining sub-module.

The pressure maintenance sub-module may be configured to apply the initial pressure maintained at the detected part of the target user. The pressure maintenance sub-module may further be configured to obtain the PPG signal and the pressure signal of the detected part of the target user maintained at a set pressure after the pressure release instruction ends.

The feature extraction sub-module may be connected to the templating processing sub-module.

The feature extraction sub-module may be configured to determine the morphological features of the PPG signal according to the template waveform of the PPG signal. The morphological features may include: an integral area of a template PPG signal, a rising edge parameter of the template PPG signal, and a difference between waveform autocorrelation and crosscorrelation of the template PPG signal.

The feature matching sub-module may be connected to the feature extraction sub-module and the pressure maintenance sub-module.

The feature matching sub-module may be configured to slidingly compare a quantitative difference of morphological features of a template waveform of a single-cycle PPG signal and morphological features of a template waveform of a PPG signal of a first cycle, and obtain an updated pressure of the pressure maintenance sub-module based on the quantitative difference.

The blood pressure update sub-module may be connected to the pressure maintenance sub-module.

The blood pressure update sub-module may be configured to obtain a new blood pressure based on the updated pressure of the pressure maintenance sub-module and a PPG signal maintained at the updated pressure.

Optionally, the initial blood pressure calculation sub-module may include: a filtering unit.

The filtering unit may be configured to optimize the initial pressure and adaptively filter the peak-to-peak value of the PPG signal.

According to the specific embodiments provided by the present disclosure, the present disclosure discloses the following technical effects:

According to the blood pressure tracking and detection system provided by the present disclosure, the pressure application and release module is configured to apply a pressure to a detected part of a target user and release the pressure on the detected part of the target user according to a pressure application instruction and a pressure release instruction. The signal obtaining module is configured to obtain a PPG signal and a pressure signal of the detected part of the target user. The blood pressure tracking and detection module is configured to determine an initial blood pressure of the detected part of the target user according to a PPG signal and a pressure signal in a pressure application and release cycle, so as to determine an initial pressure corresponding to the initial blood pressure, and obtain morphological features of the PPG signal according to the corresponding PPG signal when the pressure signal applied by the pressure application and release module to the detected part of the target user is equal to the initial pressure, so as to update the pressure according to the morphological features. It overcomes the shortcomings of an existing blood pressure tracking and detection system such as the inability to stably track and update the blood pressure for a long time, the need for frequent calibration, the need for user interaction during night tracking, and the inability to realize automatic adjustment and tracking.

BRIEF DESCRIPTION OF THE DRAWINGS

To describe the embodiments of the present disclosure or the technical solutions in the related art more clearly, the accompanying drawings required in the embodiments are briefly introduced below. Obviously, the accompanying drawings described below are only some embodiments of the present disclosure. Those of ordinary skill in the art may further obtain other accompanying drawings based on these accompanying drawings without creative labor.

DETAILED DESCRIPTION OF THE EMBODIMENTS

The technical solutions of the embodiments of the present disclosure are clearly and completely described below with reference to the accompanying drawings. Apparently, the described embodiments are merely a part rather than all of the embodiments of the present disclosure. All other embodiments obtained by those of ordinary skill in the art based on the embodiments of the present disclosure without creative efforts shall fall within the protection scope of the present disclosure.

An objective of the present disclosure is to provide a blood pressure tracking and detection system, so as to overcome shortcomings of an existing blood pressure tracking and detection system such as the inability to stably track and update the blood pressure for a long time, the need for frequent calibration, the need for user interaction during night tracking, and the inability to realize automatic adjustment and tracking.

To make the above-mentioned objective, features, and advantages of the present disclosure clearer and more comprehensible, the present disclosure will be further described in detail below in conjunction with the accompanying drawings and specific embodiments.

Figure 1:
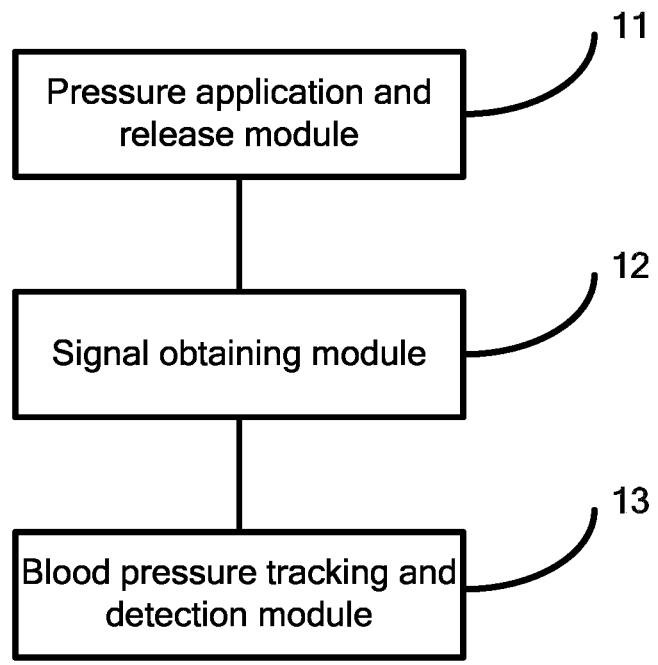
FIG. 1 is a schematic structural diagram of a blood pressure tracking and detection system provided by the present disclosure.

FIG. 1 is a schematic structural diagram of a blood pressure tracking and detection system provided by the present disclosure. As shown in FIG. 1, the blood pressure tracking and detection system provided by the present disclosure includes: a pressure application and release module 11, a signal obtaining module 12, and a blood pressure tracking and detection module 13.

The pressure application and release module 11 is configured to apply a pressure to a detected part of a target user according to a pressure application instruction. The pressure application and release module 11 is further configured to release the pressure on the detected part of the target user according to a pressure release instruction.

The signal obtaining module 12 is connected to the pressure application and release module 11. The signal obtaining module 12 is configured to obtain a PPG signal and a pressure signal of the detected part of the target user.

The blood pressure tracking and detection module 13 is connected to the signal obtaining module 12. The blood pressure tracking and detection module 13 is configured to determine an initial blood pressure of the detected part of the target user according to a PPG signal and a pressure signal in a pressure application and release cycle, so as to determine an initial pressure corresponding to the initial blood pressure, and obtain morphological features of the PPG signal according to the corresponding PPG signal when the pressure signal applied by the pressure application and release module 11 to the detected part of the target user is equal to the initial pressure, so as to update the pressure according to the morphological features.

The basic principle of the blood pressure tracking and detection system provided by the present disclosure is the constant volume method. By applying a pressure to the outside of the artery where the blood pressure is measured, the intra-arterial volume is constant when the pressure applied to the outer wall of the artery is the same as the pressure applied to the inner wall of the artery. At this time, a servo system is used to compensate the change of the intra-arterial volume caused by the change of blood pressure, such that the arterial blood vessel is in a state of constant volume. The servo system adjusts the pressure applied to the detected part of the target user in real time based on a model relationship between blood pressure changes and morphological features of pulse waves, so as to realize blood pressure tracking and detection. Blood pressure tracking and detection can be realized stably for a long time without frequent calibration and user involvement.

As a specific embodiment, the pressure application and release module 11 includes: a pressure application sub-module and a pressure release sub-module.

The pressure application sub-module is configured to apply the pressure to the detected part of the target user according to the pressure application instruction. When the pressure application instruction is executed, the pressure application sub-module pressurizes to a preset threshold and stops the application of pressure.

The pressure release sub-module is connected to the pressure application sub-module. The pressure release sub-module is configured to release the pressure on the detected part of the target user according to the pressure release instruction. When the pressure release instruction is executed, the pressure release sub-module releases the pressure to zero and stops working. The preset threshold is generally 30-50 mmHg greater than a systolic pressure of the target user. The execution of the pressure application instruction needs to end within a preset time of 10 s. The setting of the preset threshold value can achieve a significant blood flow blocking effect.

The pressure application and release module 11 further includes: a deflation speed determination sub-module.

The deflation speed determination sub-module is connected to the signal obtaining module 12. The deflation speed determination sub-module is configured to determine a peak-to-peak value of the PPG signal according to the PPG signal during deflation, and determine a deflation speed according to the peak-to-peak value of the PPG signal.

As a specific embodiment, when the peak-to-peak value does not change beyond a preset size within a set cycle, the deflation speed is a preset value, which is 2-20 mmHg/s. When the peak-to-peak value changes beyond the preset size within the set cycle, the deflation speed is adjusted to another preset value, which is 0.5-1 mmHg/s.

The adaptive adjustment of the deflation speed can accurately capture the change of the intravascular pressure in the detected part of the target user in the shortest time based on the PPG signal, so as to improve the accuracy of initial blood pressure detection and reduce the delay of initial blood pressure detection, thereby ensuring the accuracy and sensitivity of blood pressure tracking and detection of the system.

Figure 2:
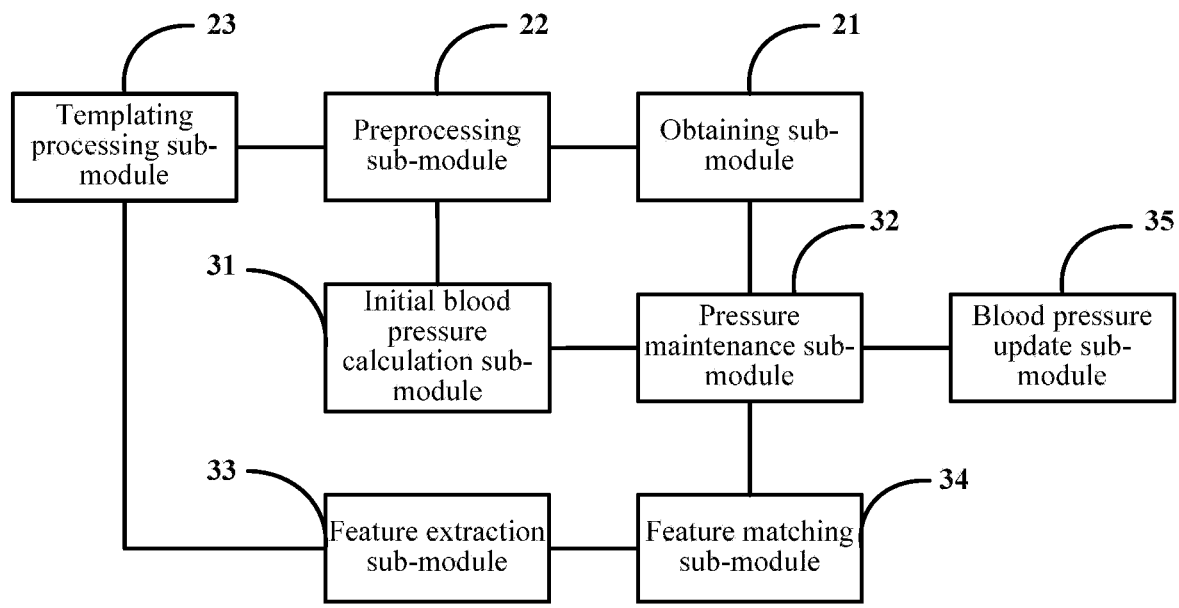
FIG. 2 is a schematic structural diagram of a signal obtaining module and a blood pressure tracking and detection module provided by the present disclosure.

As shown in FIG. 2, the signal obtaining module 12 includes: an obtaining sub-module 21, a preprocessing sub-module 22, and a templating processing sub-module 23.

The obtaining sub-module 21 is connected to the pressure application and release module 11. The obtaining sub-module 21 is configured to obtain the PPG signal and the pressure signal of the detected part of the target user.

The preprocessing sub-module 22 is connected to the obtaining sub-module 21. The preprocessing sub-module 22 is configured to perform baseline drift removal, noise filtering, envelope detection, and peak-to-peak value detection on the PPG signal.

The templating processing sub-module 23 is connected to the preprocessing sub-module 22. The templating processing sub-module 23 is configured to determine a template waveform of the PPG signal according to the preprocessed PPG signal.

In practical applications, the PPG signal is a weak signal and is very susceptible to interference. The PPG signal acquired based on the PPG method contains a lot of noise and baseline drift. In the present embodiment, the PPG baseline drift suppression and noise removal are performed by the preprocessing sub-module. After preprocessing, a clear, stable, effective and characteristic PPG signal can be obtained. The PPG signal with a high signal-to-noise ratio is the premise of obtaining accurate blood pressure parameters.

The envelope detection of the pulse wave signal includes: interpolation based on the peak of the PPG signal in a preset cycle to obtain the peak envelope; and interpolation based on the valley of the PPG signal in the preset cycle to obtain the valley envelope.

The interpolation method based on the peak in the preset cycle is cubic spline Interpolation. Cubic spline interpolation, referred to as Spline interpolation, is a smooth curve formed by a series of waveform points. Mathematically, the curve function group is obtained by solving the three bending moment equations. Definition of cubic spline function: the function is $S(x) \in C2[a,b]$, and is a cubic polynomial on each small interval $[x_j, x_{j+1}]$, where $a = x_0 < x_1 < \ldots < x_n = b$ is a given knot, then $S(x)$ is called a cubic spline function on the knots $x_0, x_1, \ldots x_n$. If the function value $Y_j = f(X_j)$, (j=0, 1, \ldots, n) is given on the knot $x_j$, and $S(x_j) = y_j$, (j=0, 1, \ldots, n) is established, then $S(x)$ is called a cubic spline interpolation function. In the actual calculation, boundary conditions need to be introduced to complete the calculation. The boundary usually has a natural boundary (the second derivative of the boundary point is 0), a clamping boundary (the derivative of the boundary point is given), and a non-kink boundary (the third derivative of the two end points is equal to the third derivative of the adjacent points of the two end points). Drawing the envelope based on the interpolation method can retain the effective information of each sampling point to the greatest extent, and improve the accuracy and validity of the blood pressure tracking and detection results.

The templating processing sub-module 23 includes: a normalization processing unit and a PPG signal template waveform determination unit.

The normalization processing unit is connected to the PPG signal template waveform determination unit.

The normalization processing unit is configured to perform single-cycle amplitude and length normalization on the preprocessed PPG signal.

The PPG signal template waveform determination unit is configured to determine the template waveform of the PPG signal according to a moving average of the PPG signal subjected to single-cycle amplitude and length normalization.

A process of performing single-cycle amplitude and length normalization on the preprocessed PPG signal includes the following steps.

The length of the preprocessed PPG signal is fixed within a preset number of points. If the waveform length in a certain cycle is greater than the preset number of points, the preset number of points is 200, and downsampling is adopted to decrease the waveform length in the cycle to the preset number of points. If the waveform length in a certain cycle is less than the preset number of points, the spline interpolation method is adopted to increase the waveform length in the cycle to the preset number of points.

A process of obtaining a moving average waveform further includes: the moving average waveform is obtained based on the moving average of the PPG signal subjected to single-cycle amplitude and length normalization within a preset cycle. The range of the preset cycle size is [3, 5]. Considering the accuracy and delay time of blood pressure tracking and detection, the average waveform in 3-5 cycles can reflect morphological changes of the pulse waveform caused by blood pressure changes more excellently, and the delay time of subsequent blood pressure detection can be controlled.

The amplitude of the single-cycle pulse wave is normalized, and the ordinates of the pulse wave are normalized to a preset finger. The length of the single-cycle pulse wave is normalized to a preset number of sampling points in a single cycle. After normalization and templating processing, individual differences caused by physiological parameters such as gender, age, and weight of users can be greatly reduced.

As shown in FIG. 2, the blood pressure tracking and detection module 13 includes: an initial blood pressure calculation sub-module 31, a pressure maintenance sub-module 32, a feature extraction sub-module 33, a feature matching sub-module 34, and a blood pressure update sub-module 35.

The initial blood pressure calculation sub-module 31 is connected to the preprocessing sub-module 22 and the pressure maintenance sub-module 32.

The initial blood pressure calculation sub-module 31 is configured to determine a pressure signal applied to the detected part of the target user corresponding to a maximum peak-to-peak difference of the preprocessed PPG signal according to the preprocessed PPG signal and the pressure signal. The pressure signal applied to the detected part of the target user corresponding to the maximum peak-to-peak difference is the initial pressure of the detected part of the target user, and an initial systolic pressure and an initial diastolic pressure of the detected part of the target user are further determined according to the initial pressure of the detected part of the target user and the pressure signal in the pressure release instruction.

The pressure maintenance sub-module 32 is connected to the obtaining sub-module 21.

The pressure maintenance sub-module 32 is configured to apply the initial pressure maintained at the detected part of the target user. The pressure maintenance sub-module 32 is further configured to obtain the PPG signal and the pressure signal of the detected part of the target user maintained at a set pressure after the pressure release instruction ends.

The feature extraction sub-module 33 is connected to the templating processing sub-module 23.

The feature extraction sub-module 33 is configured to determine the morphological features of the PPG signal according to the template waveform of the PPG signal. The morphological features include: an integral area of a template PPG signal, a rising edge parameter of the template PPG signal, and a difference between waveform autocorrelation and crosscorrelation of the template PPG signal.

The feature matching sub-module 34 is connected to the feature extraction sub-module 33 and the pressure maintenance sub-module 32.

The feature matching sub-module 34 is configured to slidingly compare a quantitative difference of morphological features of a template waveform of a single-cycle PPG signal and morphological features of a template waveform of a PPG signal of a first cycle, and obtain an updated pressure of the pressure maintenance sub-module 32 based on the quantitative difference.

The blood pressure update sub-module 35 is connected to the pressure maintenance sub-module 32. The blood pressure update sub-module 35 is configured to obtain a new blood pressure based on the updated pressure of the pressure maintenance sub-module 32 and a PPG signal maintained at the updated pressure.

The initial blood pressure calculation sub-module obtains the initial blood pressure of the finger based on the pressure application and release module 11 and the signal obtaining module 12. That is, when the external pressure on the detected part of the target user reaches a certain pressure (generally 30-50 mmHg greater than the systolic pressure), the blood flow in the blood vessel is blocked, and the PPG gradually disappears. When the pressure application sub-module reaches the threshold pressure, the pressure release sub-module releases the pressure. When the pressure reaches a certain level, the blood flow can pass through the blood vessel, and the PPG on the detected part of the target user appears again. A photoelectric sensor can detect the fluctuation of the PPG in real time. The PPG fluctuates more greatly with the gradually released pressure. Deflation is performed again, and the pulse wave fluctuation becomes smaller. A moment with the largest fluctuation is selected as a reference point. Based on this point, the pressure on the finger corresponding to a forward fluctuation point with a peak of 0.5 is the systolic pressure, the pressure on the finger corresponding to a rearward fluctuation point with a peak of 0.8 is the diastolic pressure, and the pressure corresponding to the point with the largest fluctuation is the average pressure.

Using this algorithm, the initial blood pressure of the detected part of the target user can be quickly and accurately detected, and the pressure on the detected part is low, and will not cause strong discomfort to the target user. In addition, the correct initial pressure can be provided for the pressure maintenance sub-module 32, which ensures the initial accuracy of blood pressure tracking and detection.

When the external pressure on the detected part of the target user is maintained at a pressure equal to the initial average pressure, the fluctuation intensity of the PPG is the largest, so the change of its morphological features will show the optimal tracking effect with the change of blood pressure.

The morphological features of the PPG signal subjected to templating processing are extracted as follows.

Based on the valley and peak of the template waveform of the PPG signal, a valley-to-peak connection line is linearly fitted, and the area of the closed area enclosed by the connection line and the rising edge of the pulse wave is the rising edge parameter of the template PPG signal.

Based on the valley and peak of the template waveform of the PPG signal, a cycle from one valley to another is defined as a PPG signal cycle. ⅓ of the difference between the peak and valley of the PPG signal is taken as the baseline in each cycle. The PPG signal is divided into an upper half wave and a negative half wave. The area difference of the closed area of the upper half wave and the negative half wave of the baseline is defined as an integral area of the template PPG signal.

Based on the template waveform of the PPG signal, first, the 1st template waveform of the PPG signal is subjected to autocorrelation analysis to obtain a corresponding autocorrelation matrix. Then, the i-th templated waveform and the 1st template waveform of the PPG signal are subjected to crosscorrelation analysis in a circular cycle to obtain a crosscorrelation matrix. Based on the difference between the i-th crosscorrelation matrix and the 1st autocorrelation matrix, the difference between the i-th template waveform of the PPG signal and the 1st template waveform of the PPG signal can be reflected. Through the autocorrelation and crosscorrelation data processing methods, useful information hidden in cluttered signals can be found. This ability is very important, because the signals in engineering practice are inevitably subject to various interferences, and in severe cases, the really useful data will be completely submerged. Through autocorrelation, repetitive information (periodic signals masked by noise) can be found, or fundamental frequencies hidden in the harmonic frequencies of the signal can be identified, and it is often used in the analysis of time-domain signals.

Figure 3:
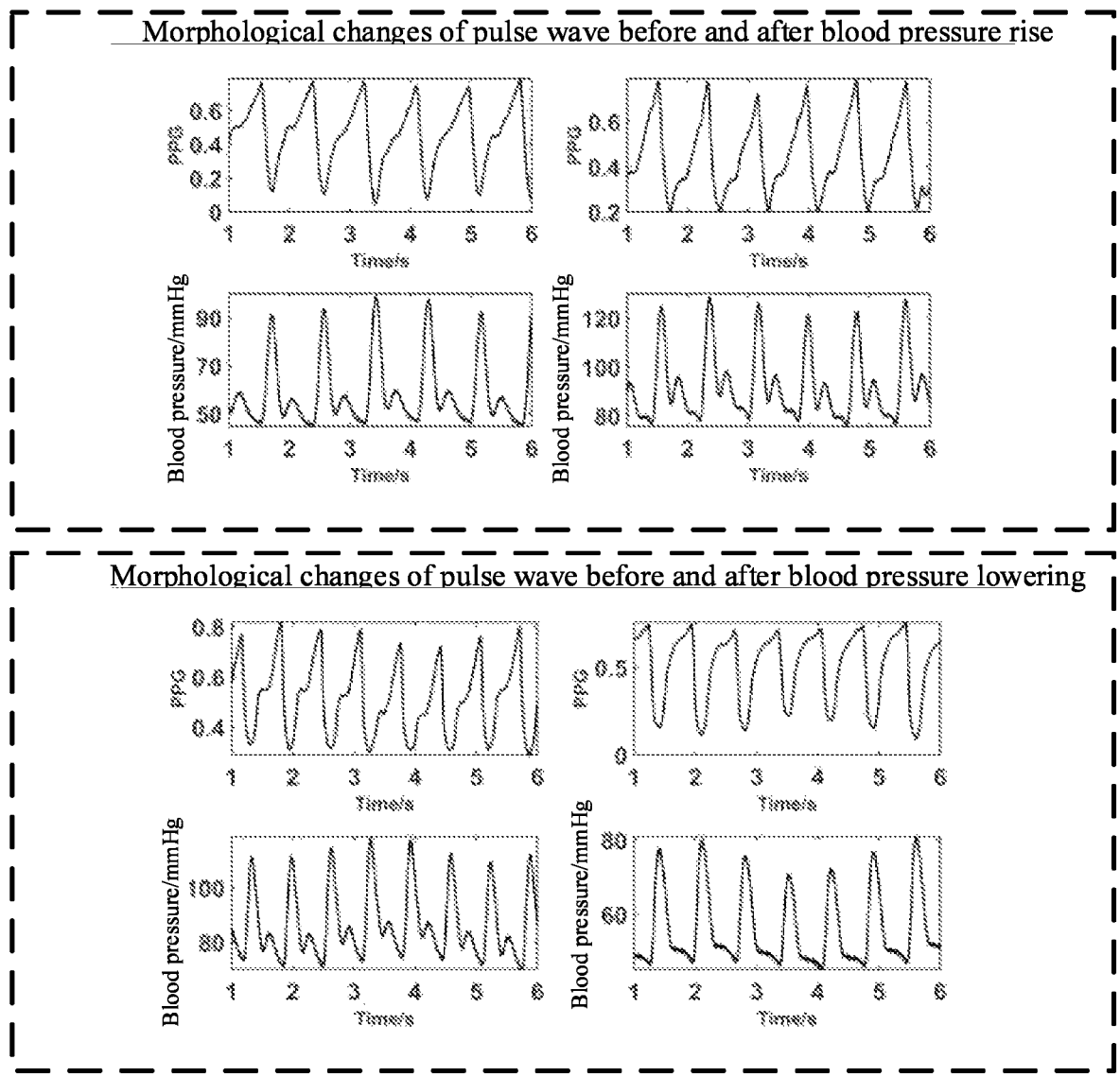
FIG. 3 is a schematic diagram of a blood pressure change process.

As shown in FIG. 3, during the blood pressure change, with the blood pressure change, the morphology of the pulse wave will change significantly. Through the blood loss and blood transfusion experiments in animal experiments, a pressure equal to the initial average pressure is applied to the tail of the animal through the above solution, and the features of the pulse waveform of the tail of the animal are compared with those of the actual blood pressure waveform. It can be found that in the process of blood pressure from low to high, the morphology of the pulse wave will change from normal to thin and high. In the process of blood pressure from high to low, the morphology of the pulse wave will change from normal to fat and wide. The process can prove that in the blood pressure tracking and detection, the pulse wave applied under the average pressure will obviously change with the change of blood pressure, and it has the morphological reliability of the physiological signal.

In order to remove the abnormal situation of the peak-to-peak value of the PPG signal caused by the movement of the target user, and further improve the accuracy of the initial blood pressure detection, the initial blood pressure calculation sub-module 31 includes: a filtering unit.

The filtering unit is configured to optimize the initial pressure and adaptively filter the peak-to-peak value of the PPG signal.

The feature matching sub-module 34 further includes: updating the pressure of the pressure maintenance sub-module 32 is to restore the morphology of the PPG signal to the template morphology of the first initial PPG signal, that is, the morphology of the PPG signal under the current average pressure.

Figure 4A:
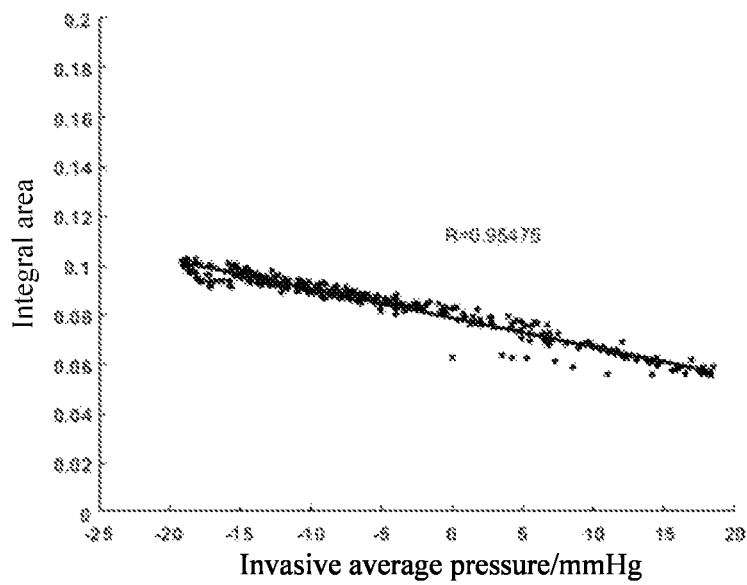
FIG. 4A-C are schematic diagrams showing a relationship between morphological features of three PPG signals and blood pressure changes.
Figure 4B:
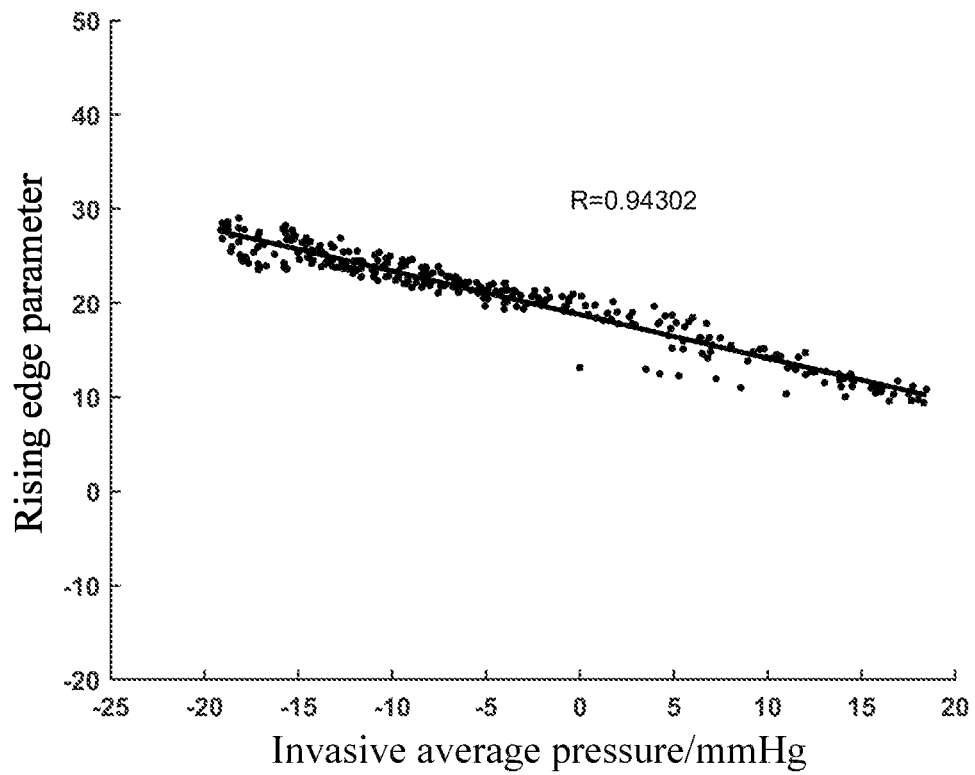
Figure 4C:
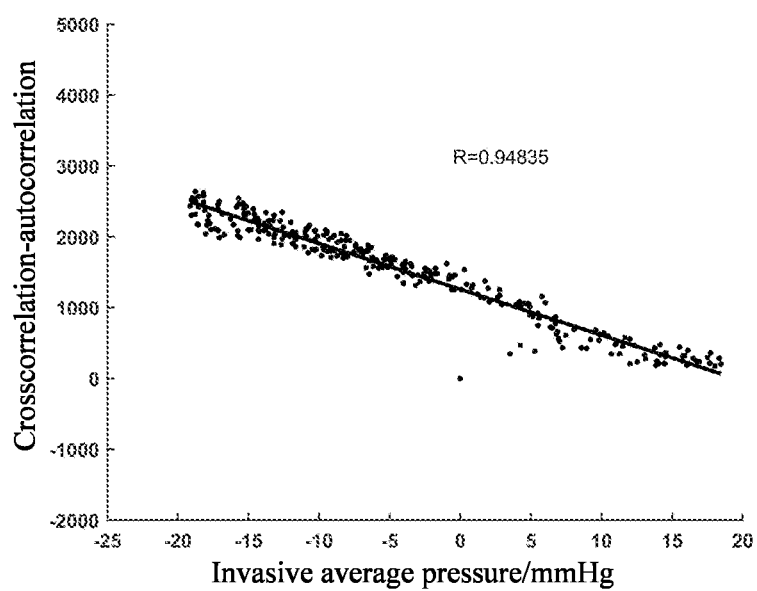

FIG. 4A-C shows the relationship between morphological features of three PPG signals and blood pressure changes. With the increase of blood pressure, the parameters show a strong negative correlation, and the correlations are all greater than 90%. The morphological eigenvalues of the PPG signal have statistical and physiological significance in blood pressure tracking and detection. When blood pressure changes, reliable predictors play a key role, which can timely feedback the blood pressure trend and perform accurate tracking. In addition, the extraction algorithm of this feature can also be transplanted into embedded products, which lays a foundation for the realization of blood pressure tracking and detection products.

Each embodiment of the present specification is described in a progressive manner, each embodiment focuses on the difference from other embodiments, and the same and similar parts between the embodiments may refer to each other.

In this specification, some specific examples are used for illustration of the principles and implementations of the present disclosure. The description of the foregoing embodiments is used to help illustrate the method of the present disclosure and the core ideas thereof. In addition, those of ordinary skill in the art can make various modifications in terms of specific implementations and the scope of application in accordance with the ideas of the present disclosure. In conclusion, the content of the present description shall not be construed as limitations to the present disclosure.

What is claimed is:

1. A blood pressure tracking and detection system, comprising:
    a sphygmomanometer for applying a pressure to a detected part of a target user according to a pressure application instruction, and releasing the pressure on the detected part of the target user according to a pressure release instruction,
    a signal obtaining module connected to the sphygmomanometer for obtaining a photoplethysmography (PPG) signal and a pressure signal of the detected part of the target user,
    wherein the signal obtaining module comprises:
    a photo sensor and a pressure sensor for obtaining the PPG signal and the pressure signal of the detected part of the target user and at least one signal processor for executing operations, wherein the at least one signal processor is configured to perform each of baseline drift removal, noise filtering, envelope detection, and peak-to-peak value detection via cubic spline Interpolation on the PPG signal to obtain preprocessed PPG signal; and
    wherein the at least one signal processor is further configured to determine a template waveform of the PPG signal according to the preprocessed PPG signal, the at least one signal processor comprising a blood pressure tracking and detection module connected to the signal obtaining module, wherein the blood pressure tracking and detection module comprises at least one tracking processor and a memory storing instructions that, when executed by the at least one tracking processor, cause the at least one tracking processor to execute operations comprising:

performing a pressure signal of the detected part of the target user corresponding to a maximum peak-to-peak difference of the preprocessed PPG signal according to the preprocessed PPG signal and the pressure signal, wherein the pressure signal of the detected part of the target user corresponding to the maximum peak-to-peak difference is the an initial pressure of the detected part of the target user, and an initial systolic pressure and an initial diastolic pressure of the detected part of the target user are further determined according to the initial pressure of the detected part of the target user and the pressure signal in the pressure release instruction, applying the initial pressure maintained at the detected part of the target user, and obtains obtaining the PPG signal and the pressure signal of the detected part of the target user maintained at a set pressure after the pressure release instruction ends, determining the morphological features of the PPG signal according to the template waveform of the PPG signal, and wherein the morphological features comprise:

an integral area of a template PPG signal, a rising edge parameter of the template PPG signal, and a difference between waveform autocorrelation and cross-correlation of the template PPG signal;

further, slidingly comparing a quantitative difference of morphological features of a template waveform of a single-cycle PPG signal and morphological features of a template waveform of a PPG signal of a first cycle, and obtaining an updated pressure based on the quantitative difference, and obtaining a new blood pressure based on the updated pressure and a PPG signal maintained at the updated pressure.

2. The blood pressure tracking and detection system according to claim 1, wherein the sphygmomanometer is further configured to determine a peak-to-peak value of the PPG signal according to the PPG signal during deflation, and determine a deflation speed according to the peak-to-peak value of the PPG signal.

3. The blood pressure tracking and detection system according to claim 1, wherein the at least one signal processor is further configured to
- perform single-cycle amplitude and length normalization on the preprocessed PPG signal, and
- determine the template waveform of the PPG signal according to a moving average of the PPG signal subjected to single-cycle amplitude and length normalization.

4. The blood pressure tracking and detection system according to claim 1, wherein the blood pressure tracking and detection module further comprises a filter for optimizing the initial pressure and adaptively filtering the peak-to-peak value of the PPG signal.

* * * * *